United States Patent
Larrick et al.

(10) Patent No.: US 8,101,199 B2
(45) Date of Patent: Jan. 24, 2012

(54) DES-METHYL-TOCOPHEROL THERAPY FOR RESTENOSIS PREVENTION

(75) Inventors: James W. Larrick, Mountain View, CA (US); James C. Peacock, III, San Carlos, CA (US)

(73) Assignee: Celonova Biosciences, Inc., San Antonio, TX (US)

( * ) Notice: Subject to any disclaimer, the term of this patent is extended or adjusted under 35 U.S.C. 154(b) by 1581 days.

(21) Appl. No.: 10/595,453

(22) PCT Filed: Oct. 21, 2004

(86) PCT No.: PCT/US2004/035361
§ 371 (c)(1),
(2), (4) Date: Apr. 28, 2006

(87) PCT Pub. No.: WO2005/039443
PCT Pub. Date: May 6, 2005

(65) Prior Publication Data
US 2007/0014827 A1   Jan. 18, 2007

Related U.S. Application Data

(60) Provisional application No. 60/513,299, filed on Oct. 21, 2003.

(51) Int. Cl.
*A61F 2/02* (2006.01)
(52) U.S. Cl. ...................................................... 424/423
(58) Field of Classification Search .......................... None
See application file for complete search history.

(56) References Cited

U.S. PATENT DOCUMENTS

| | | |
|---|---|---|
| 6,569,441 B2 | 5/2003 | Kunz et al. |
| 2002/0165268 A1 | 11/2002 | Wechter |
| 2003/0077312 A1 | 4/2003 | Schmulewicz et al. |

FOREIGN PATENT DOCUMENTS

| | | |
|---|---|---|
| WO | 99/25336 A1 | 5/1999 |
| WO | 03/039612 A2 | 5/2003 |

(Continued)

OTHER PUBLICATIONS

Tardiff, "Clinical results with AGI-1067: A novel Antioxidant Vascular Protectant", American Journal of Cardiology, vol. 91, Issue 3, Supplement, pp. 41-49, Feb. 6, 2003.*

(Continued)

*Primary Examiner* — Carlos Azpuru
(74) *Attorney, Agent, or Firm* — Rissman Hendricks & Oliverio LLP

(57) ABSTRACT

A stent is provided in combination with delivery of a tocopherol agent, and in particular a des-methyl tocopherol agent, and further beneficially a gamma-tocopherol agent, so as to reduce restenosis along the vessel or other lumenal wall where the stent is implanted. In particular applications, the stent is an endolumenal stent, and more specific beneficial applications is an endovascular stent, and the gamma-tocopherol elutes from a coating or carrier coupled with the stent. Certain combinations are provided with the des-methyl-tocopherol or phytyl substituted chromanol, e.g. gamma-tocopherol, combined with an additional agent such as an anti-restenosis agent, e.g. sirolimus, tacrolimus, everolimus, or paclitaxel, in order to provide synergistic benefit to tissues along the stented or recanalized regions. Other forms of tocopherol or tocotrienol, or other phytyl substituted chromanols, and other compounds such as palm oil, are also contemplated, for use to treat restenosis.

19 Claims, 1 Drawing Sheet

FOREIGN PATENT DOCUMENTS

| WO | 03/045582 A1 | 5/2003 |
|---|---|---|
| WO | 03/053407 A1 | 7/2003 |
| WO | 03/072159 A1 | 9/2003 |

OTHER PUBLICATIONS

Blann et al. "Free radicals, antioxidants, and endothelial cell damage after percutaneous transluminal coronary angioplasty." Coron Artery Dis. Oct. 1993;4(10):905-10. PubMed PMID: 8269197.

Demaio et al. "Vitamin E supplementation, plasma lipids and incidence of restenosis after percutaneous transluminal coronary angioplasty (PTCA)." J Am Coll Nutr. Feb. 1992;11(1);68-73. (Andreas Gruentzig Cardiovascular Center, Department of Internal Medicine (Cardiology), Atlanta, GA).

Deng et al. "Probucol protects against smooth muscle cell proliferation by upregulating hehe oxygenase-1" Circulation, Sep. 28, 2004; 110(13):1855-60. Epub Sep. 13, 2004.

Ferns et al. "Probucol inhibits neointimal thickening and macrophase accumulation after balloon injury in the cholesterol-fed rabbit." Proc. Natl. Acad. Sci., 89:11312-11316, Dec. 1992.

Freyschuss et al. "Antioxidant Treatment Inhibits the Development of Intimal Thickening after Balloon Injury of the Aorta in Hypercholesterolemic Rabbits." J. Clin. Invest., 92:1282-1288, 1993.

Godfried et al. "Potentiation of atherosclerotic lesions in rabbits by a high dietary level of vitamin E." British Journal of Nutrition, May, 1989;61(3):607-17. Pub Med PMID: 2758015.

Jiang et al. "Gamma-tocopherol, the major form of vitamin E in the US diet, deserves more attention." Am. J. Clin. Nutr., Dec. 2001;74(6):714-22.

Konneh et al. "Vitamin E inhibits the intimal response to balloon catheter injury in the carotid artery of the cholesterol-fed rat." Atherosclerosis. Feb. 1995;113(1):29-39. PubMed PMID: 7755653.

LaFont et al. "Effect of alpha-tocopherol on restenosis after angioplasty in a model of experimental atherosclerosis." J. Clin. Invest., Mar. 1995;95(3):1018-25.

Leaf et al. "Do fish oils prevent restenosis after coronary angioplasty?" Circulation, Nov. 1994; 92(5):2247-57. (Massachusettes General Hospital, Charlestown 02129).

Nunes et al. "Combination of Vitamins C and E Alters the Response to Coronary Balloon Injury in the Pig." Arteriosclerosis, Thrombosis, and Vascular Biology, (1005), vol. 15, No. 1, pp. 156-165.

Ong et al. "Palm oil: a healthful and cost-effective dietary component." Food Nutr Bull. Mar. 2002;23(1):11-22. Review. PubMed PMID: 11975364.

Rodes et al. "Prevention of restenosis after angioplasty in small coronary arteries with probucol." Circulation, Feb. 10, 1998; 97(5):429-36.

Schneider et al. "Probucol Decreases Neointimal Formation in a Swine Model of Coronary Artery Balloon Injury." Basic Science Report, 88:628-637, 1993.

Tardif et al. "Probucol and Multivitamins in the Prevention of Restenosis after Coronary Angioplasty." The New England Journal of Medicine, 337:365-372, 1997.

Tardif "Insights into oxidative stress and atherosclerosis." Can J Cardiol. Jul. 2000;16 Suppl D:2D-4D. Review. PubMed PMID: 10932028.

Tardif et al. "Prevention of restenosis with antioxidants: mechanisms and implications." Am J Cardiovasc Drugs. 2002;2(5):323-34. Review. PubMed PMID: 14727962.

Tardif "Clinical results with AGI-1067: a novel antioxidant vascular protectant." Am J Cardiol. Feb. 6, 2003;91 (3A):41A-49A. Review. PubMed PMID: 12645643.

\* cited by examiner

DES-METHYL-TOCOPHEROL THERAPY FOR RESTENOSIS PREVENTION

CROSS-REFERENCE TO RELATED APPLICATIONS

The present application is a United States national phase application under 35 U.S.C. §365 of International Application No. PCT/US2004/035361 filed on Oct. 21, 2004, and claims priority to Provisional Patent Application Ser. No. 60/513,299, filed on Oct. 21, 2003, which are herein incorporated in its their entirety by reference thereto.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention is a system and related methods of manufacture and use that combine medical device implants with bioactive agent delivery. More specifically, it is an implantable stent system and related methods of use. Still more specifically, it is a system that includes an implantable stent in combination with gamma-tocopherol agent delivery.

2. Description of Related Art

Implantable stents have been under significant development for more than a decade, and many different designs have been investigated and made commercially available for use in providing mechanical scaffolding to hold body lumens, including in particular blood vessels, and more specifically coronary and peripheral arteries. Other body lumens where stents have been disclosed for use include pulmonary veins, gastro-intestinal tract, biliary duct, fallopian tubes, and vas deferens. Still further, artificial lumens have been created in the body in a man-made effort to provide artificial communication or transport within the body, such as for example shunts, and transmyocardial revascularization, and stents have been disclosed for intended use in these lumens as well.

Vascular stents are generally tubular members formed from a lattice of structural struts that are interconnected to form an integrated strut network that forms a wall that surrounds an axis. The integrated strut lattice typically includes inter-strut gaps through which the inner lumenal axis within the stent wall and outer region surrounding the stent wall are able to communicate. This is beneficial for example in the setting of stent implantation along a length of a main lumen, e.g. an artery, where side branches may beneficially receive flow from the main lumen through the gaps in the stent wall.

The majority of commercially available stents form completely integrated tubular structures, with continuity found along the integrated strut lattice both circumferentially as well as longitudinally. In order to provide for the adjustability between the collapsed and expanded conditions, such stents generally incorporate undulating shapes for the struts, which shapes are intended to reconfigure to allow for maximized radial expansion with minimized longitudinal change along the stent length. This is generally desirable for example in order to achieve repeatable, predictable placement of the stent along a desired length of localized, diseased region to be re-opened (e.g. occlusion), as well as maintain stent coverage over the expanding balloon at the balloon ends. Else, a stent that substantially shortens during balloon expansion exposes the balloon ends to localized vessel wall trauma at those ends without the benefit of the stent scaffolding to hold those regions open long-term after the intervention is completed.

Notwithstanding the prevalence of the foregoing type of stent just described, other designs have also been disclosed that either further modify such general structures, or further depart from the basic design. For example, one additional type of stent forms a wall that is not circumferentially continuous, but has two opposite ends along a sheet formed from the strut lattice. This sheet is adjusted to the collapsed condition by rolling the stent from one end to the other. At the site of implantation, the stent is unrolled to form the structural wall that radially engages the lumenal wall and substantially around an inner lumen. In the event the stent is undersized to the lumen, the opposite ends overlap and thus double the thickness of implant material that protrudes from the lumen wall and into the lumen. In another example, stents have been disclosed that form a helical structure along a vessel wall when implanted, which approach has been in particular promoted for beneficial treatments of peripheral vessels such as superficial femoral artery (SFA) implants due to resistance to kinking during stress of axial or longitudinal movement.

Stents are most frequently used in an interventional recanalization procedure, adjunctive to methods such as balloon angioplasty, or atherectomy such as rotational atherectomy devices and methods. "Balloon expandable" stents are generally constructed from a material, such as stainless steel or cobalt-chromium alloy for example, that is sufficiently ductile to be delivered in a collapsed condition on an outer surface of a deflated balloon, and is then expandable by inflation of the balloon to an expanded condition against the subject lumenal wall and that is substantially retained in such condition as an implant upon subsequent balloon deflation. "Self-expanding" stents are generally constructed of an elastic, super-elastic or shape-memory material, such as particular metal alloys including for example nickel-titanium alloys. These materials typically have a memory state that is expanded, but is delivered to the implantation site in a collapsed condition for appropriate delivery profiles. Once in place, the stent is released to recover or "self-expand" against the lumenal wall where it is then left as the implant.

Stents are typically intended to maintain patency, other uses have been disclosed. For example, some stents have been disclosed for the purpose of occluding the subject lumen where the stent is implanted. Examples of such stents include fibrin coated stents, and examples of such occlusive uses for stents include fallopian tubal ligation and aneurysm closure.

Stents have been further included in assemblies with other structures, such as grafts to form "stent-grafts". These assemblies generally incorporate a stent structure that is secured to a graft material, such as formed from a textile or sheet material type construction. Examples of uses that have been disclosed for stent-grafts include for example aneurysm isolation, such as in particular along the abdominal aorta wall.

In the particular setting of vascular stenting, stents have had an enormous impact upon the occurrence of "restenosis" following recanalization procedures. "Restenosis" is a re-occlusion of the acutely recanalized blockage that typically takes place within 3-6 months after intervention, and is generally a combination of mechanical and physiological responses to the vessel wall injury caused by the recanalization procedure itself. In one regard, restenosis can occur at least in part from an elastic recoil of the expanded vessel wall, such as following expansion of the wall during balloon angioplasty. With respect to the physiological response to injury, it has generally been observed that injury from the recanalization to the intimal, medial, and sometimes adventitial layers of a vessel wall causes smooth muscle cells within the wall to undergo aggressive mitosis and hyperproliferation, dividing and migrating into the vessel lumen to form a "scar" that occludes the vessel lumen. Whereas angioplasty and other recanalization interventions prior to the advent of stenting resulted in approximately 30%-50% restenosis rate, stenting has generally reduced this rate to about 20%-30%, which reduction is considered at least in part a result of the mechanical prevention of vascular recoil.

Recent efforts in vascular stenting have been intended to incorporate additional therapy adjunctive to stenting to further reduce the incidence of restenosis. Some efforts for example have been intended to locally deliver therapeutic doses of radiation to the vessel wall concomitant to stenting, including for example by incorporating radioactive materials into or on the stent scaffolding itself. However, these efforts carry significant burden peri-operatively in handling and disposing of the materials, and results have yet to be considered compelling among substantial portions of the healthcare community. Moreover, local energy delivery such as via radioactive stents is substantially different than local elution delivery of materials and compounds from stents which are thereafter subject to diffusion, flow, and other active transport mechanisms.

More recently, a substantial industry effort has been underway to incorporate local drug delivery to stented lesions specifically to retard and prevent restenosis. A molecular approach is considered a highly beneficial solution for the restenosis problem (Sousa et al. Circ 2003; 107:2274-2279). For example, various local delivery devices have been disclosed to provide highly localized injection of anti-restenosis material into the injured wall, such as via micro-needles incorporated onto the outer skin of expandable balloons.

A more substantial effort, however, has been to incorporate the anti-restenosis drugs on or into the stents themselves in a manner such that the stent elutes the drug into the vessel wall over a prescribed period of time following implantation, otherwise known as drug eluting stents ("DES"). Examples of devices intended for this use include coated stents, which provide a stent structure with an outer coating that holds and elutes the drug.

The most prevalent form of coatings disclosed for use in DES devices include polymers, such as for example in one particular commercial embodiment a two-layer polymer coating with one layer holding drug and another layer retarding elution to provide drug release over an extended period of time, or with one layer providing adhesion to the underlying stent metal and the other layer holding and eluting the drug. Other examples of DES coatings include ceramics, hydrogels, biosynthetic materials, and metal-drug matrix coatings.

Examples of drugs that have been investigated for anti-restenosis uses such as via DES methods include anti-mitotics, anti-proliferatives, anti-inflammatory, and anti-migratory compounds. Further examples of compounds previously disclosed for use in DES devices and methods include: angiotensin converting enzyme (ACE) inhibitors, angiotensin receptor antagonists, anti-sense materials, anti-thrombotics, platelet aggregation inhibitors, iron chelators (e.g. exochelin), everolimus, tacrolimus, vasodilators, nitric oxide, and nitric oxide pressors or promoters.

Two more specific compounds that have been under substantial clinical investigation on DES devices include sirolimus and paclitaxel. These DES efforts have made substantial strides toward reducing restenosis rates from the typical rate in stented lesions of about 20% to about 35%, to a reduced rate generally around, or in some populations possibly below, about 10%.

Notwithstanding the substantial improvements that appear to be anticipated in view of the recent sirolimus and paclitaxel DES clinical experiences, however, various concerns still remain and various needs also still remain that with respect to these and other previously disclosed DES efforts. For example, the reduced restenosis rates experienced may be driven lower with drugs with still more potent efficacy. Moreover, concerns remain regarding other possible harmful effects of the interventional drug approaches which block aspects of the smooth muscle cell cycle, e.g. toxicity, weakening of the vessel lining, late loss, negative remodeling, and possible aneurysm formation.

In one regard, certain drugs have been promoted for such use in preventing restenosis by virtue of their "pro-healing" bioactivity, often associated with promoting re-endothelialization of the injured region of lumen where the stent is implanted. More specifically, during stent placement in blood vessels, the vessel injury that typically initiates the cascade of events of the restenosis cycle includes denudation of the endothelium along the vessel lining. Endothelium lines the vessel wall and provides, among other things, a barrier between the smooth muscle cell lining of the vessel wall and various factors within blood pool of the inner lumen. Once denuded of the endothelium, and frequently also concomitant with breaking of an elastic lamina barrier between the endothelium and media/adventitia, these factors are exposed to the muscle cells and initiate the restenosis cascade to mitosis, migration, and hyper-proliferation into the vessel. Accordingly, promoting re-endothelialization, and hence re-establishing the barrier against the restenosis pressors from the blood pool, has been promoted as a viable, less traumatic, and highly advantageous approach to preventing restenosis. Moreover, by preventing the proliferation via healing from rapid re-endotheliazation, many side effects concomitant with various cytotoxic or other "anti-proliferative" agent approaches are avoided, including for example weakening of the wall, negative remodeling, and possible aneurysm formation, are avoided.

One example of a "pro-healing" approach intended to treat restenosis includes delivering VEGf as a growth factor to promote endothelialization of an injured vessel wall. Another example of a "pro-healing" approach intended to promote re-endothelialization over a stent provides anti-bodies on a stent surface which are intended to attract adhesion of endothelium. None of these approaches have yet been shown to provide sufficient safety and efficacy to prevent restenosis to be advanced to widespread commercial use. Other approaches to promote "re-endothelialization" of stented vessels would provide substantial benefit to patients and healthcare in general.

Pleiotrophin (PTN) is another growth factor that has been previously investigated for promoting angiogenesis and has also been observed as a potent agent to promote self-limiting tissue proliferation, and in particular regard to endothelium, believed useful for "wound healing" applications. Incorporation of this growth factor with stenting procedures and otherwise for vascular healing, e.g. endothelialization of vascular or other lumen linings to heal wall injury and prevent restenosis, is considered a substantial benefit.

Notwithstanding the wide variety of compounds that have or are being investigated for restenosis therapy/prevention, presently approved drugs for preventing restenosis are generally considered toxic compounds. Each presents substantial risk of certain undesirable effects aside from the benefit afforded by their local delivery. A substantial goal of restenosis prevention via stent delivery in particular is to prevent the restenotic response with as low a dose as possible, while preventing other harmful effects such as vessel remodeling, thrombosis, inflammation, allergic reaction, cellular apoptosis, etc. In this regard, more pro-healing approaches and related compounds have become the topic of substantial investigation, but have yet to be approved or used in mainstream medicine. In another regard, combined delivery of multiple compounds in "cocktail" formulation has also become an interesting topic of investigation. In particular, certain anti-inflammatory agents have been investigated for stent elution in combined form with other potent anti-proliferative or anti-mitotic compounds.

Vitamin E is a compound that has been variously disclosed in the past related to wound healing, and in particular protection against keloid scarring, a hyperproliferative response to injury that shares certain biochemical similarities with vascular restenosis. Vitamin E is remarkably safe, and falls within a class of compounds that are "generally regarded as safe" or "GRAS". Vitamin E is available in several forms that present varied activities between them. Whereas alpha-tocopherol has been widely investigated for therapeutic uses, until recently gamma-tocopherol (a form of "des-methyl tocopherol") has received much less attention in science. However, gamma-tocopherol presents a variety of beneficial advantages over alpha-tocopherol in various considerations. In one particular regard, gamma-tocopherol has been characterized to exhibit much more potent anti-oxidant qualities, resulting in a unique anti-inflammatory activity not shared with the alpha-tocopherol. In addition, gamma-tocopherol is believed to enhance outcomes of therapy when combined with certain other bioactive agents or drugs. Notwithstanding these beneficial characteristics, gamma-tocopherol has not heretofore been disclosed for use as a therapeutic agent for treating restenosis or otherwise for delivery via or with stents, either alone or in combination with other bioactive agents.

A need remains for local delivery of safe and efficacious anti-inflammatory and healing agents to treat abnormal lumenal wall conditions.

A need remains in particular for local delivery of such a compound so as to promote wound healing of blood vessels and other lumens in response to injury, such as associated with recanalization or stent implantation interventions.

Much benefit may be provided by delivering gamma-tocopherol, or a precursor, analog, or derivative thereof, or another compound sharing similar characteristics with gamma-tocopherol, to injured lumenal walls following endolumenal stent implantation or otherwise in order to provide local therapy to adverse lumenal wall conditions.

BRIEF SUMMARY OF THE INVENTION

Accordingly, one aspect of the invention is a method which delivers gamma-tocopherol, or an analog or derivative thereof, to an injured region of a luminal wall in order to promote healing thereof.

Another aspect of the invention is a method that delivers gamma-tocopherol, or an analog or derivative thereof, to an injured region of a luminal wall in order to substantially prevent restenosis thereof.

Another aspect of the invention is a medical device system that includes an implantable stent in combination with gamma-tocopherol or an analog or derivative thereof.

Another aspect of the invention is a method that includes delivering a stent to a region of a body space, and also delivering gamma-tocopherol or an analog or derivative thereof to that stented region.

Another aspect of the invention is a method that includes delivering a growth factor to an injured region of a body lumen such that healing of the injured region is promoted and substantial occlusion of the body lumen is prevented.

Another aspect of the invention is a method that includes delivering a GRAS compound to a stented region of a blood vessel such that endothelialization of the stent and stented region is promoted and restenosis of the stented region is substantially prevented.

Another aspect of the invention is a system for initiating or promoting vascular wound healing that includes a bioactive agent in a delivery carrier that is part of a vascular interventional device. In particular regard to this system, the bioactive agent includes at least one of a des-methyl-tocopherol agent and a phytyl substituted chromanol agent.

According to one mode of this aspect, the vascular interventional device comprises a stent that is adapted to hold and elute the gamma-tocopherol agent.

According to one embodiment of this mode, the stent is coated or adsorbed with the delivery carrier containing the bioactive agent. According to another embodiment, the stent is adapted to elute the bioactive agent.

In another mode, the vascular interventional device includes an angioplasty balloon.

In another mode, the bioactive agent includes a tocopherol plasmid, such as for gamma-tocopherol.

In another mode, the bioactive agent is or includes a tocopherol gene vector, such as for gamma-tocopherol.

Another aspect of the invention is an implantable endolumenal stent system that includes an implantable endolumenal stent with a volume of bioactive gamma-tocopherol agent coupled to the stent. In particular to this aspect, the endolumenal stent is adapted to elute the volume of gamma-tocopherol into surrounding tissue when the endolumenal stent is implanted along a lumen within a patient.

Another aspect of the invention is a drug eluting stent system that includes a stent and a bioactive agent coupled to the stent. The stent is adapted to elute the bioactive agent into surrounding lumenal wall tissue when implanted along the lumen within a body of a patient. In particular to this aspect, the bioactive agent includes at least one of a des-methyl tocopherol agent and a phytyl substituted chromanol agent.

Another aspect of the invention is a lumenal wall therapy system that includes a delivery system and a pharmaceutically acceptable preparation of a bioactive agent that includes at least one of a des-methyl tocopherol agent and a phytyl substituted chromanol agent. The delivery system is adapted to deliver a therapeutic dose of the bioactive agent to a location along a lumenal wall of a lumen within a body of a patient.

Another aspect of the invention is a drug eluting stent system that includes a stent and a bioactive agent coupled to the stent. The stent is adapted to elute the bioactive agent into surrounding lumenal wall tissue when implanted along the lumen within a body of a patient. The bioactive agent includes a pharmaceutically acceptable preparation of palm oil, or a precursor, analog, or derivative thereof.

Another aspect of the invention is a lumenal wall therapy system that includes a delivery system and a pharmaceutically acceptable preparation of a bioactive palm oil agent, or a precursor, analog, or derivative thereof. The delivery system is adapted to deliver a therapeutic dose of the bioactive agent to a location along a lumenal wall of a lumen within a body of a patient.

According to one further mode of the various aspects herein described, the bioactive agent being therapeutically delivered to treat abnormal lumenal wall tissue conditions includes a form of des-methyl tocopherol.

According to another further mode of these aspects, the bioactive agent includes in particular a gamma-tocopherol agent, or a precursor, analog, or derivative thereof.

According to another such further mode, the bioactive agent includes a delta-tocopherol agent, or a precursor, analog, or derivative thereof.

According to another such further mode, the bioactive agent includes a phytyl substituted chromanol agent.

According to another such further mode, the bioactive agent includes a gamma-tocotrienol agent, or a precursor, analog, or derivative thereof.

According to another such further mode, the bioactive agent includes a delta-tocotrienol agent, or a precursor, analog, or derivative thereof.

According to another such further mode, the bioactive agent includes a combination of two separate agents, wherein one of the agents comprises a des-methyl tocopherol agent, and the other of the agents comprises a phytyl substituted chromanol agent.

According to another such further mode, a porous metal carrier matrix is also provided. The bioactive agent is located principally within the porous metal carrier matrix and is adapted to elute therefrom into tissue in contact with the porous metal carrier matrix.

In one embodiment of this mode, the porous metal carrier matrix comprises a sintered metal matrix.

In another embodiment of this mode, the porous metal carrier matrix comprises a sputtered metal matrix.

In another embodiment, the porous metal carrier matrix comprises an electrochemically deposited matrix.

In another embodiment, the porous metal carrier matrix comprises an electrolessly electrochemically deposited matrix.

In another mode, the bioactive agent includes a first bioactive agent, and the system further includes a second bioactive agent that is different from the first agent. The second bioactive agent is adapted to be delivered into tissue in combination with the first bioactive agent.

According to one embodiment of this mode, the second bioactive agent comprises at least one of sirolimus, tacrolimus, everolimus, ABT-578, paclitaxel, dexamethasone, 17-Beta-estradiol, steroid, des-aspartate angiotensin I (DAA-1), angiotensin converting enzyme inhibitor (ACE inhibitor), angiotensin II receptor blocker, tachykinin, sialokinin, apocynin, pleiotrophin, exochelin, an iron chelator, VEGF, heparin, coumadin, clopidogrel, IIb/IIIa inhibitor, nitric oxide, a nitric oxide donor, an eNOS antagonist, a nitric oxide synthesis promoter, a statin, or a precursor, analog, or derivative thereof, or a combination or blend thereof.

According to another mode of the various aspects hereunder, the bioactive agent includes a pharmaceutically acceptable preparation of red palm oil agent, or a precursor, analog, or derivative thereof.

Another aspect of the invention is a method for stimulating or promoting vascular wound healing of an endovascular wall injury caused during a vascular interventional procedure. This method includes delivering a pharmaceutically acceptable preparation of a bioactive tocopherol agent to the endovascular wall injury. In particular according to this method, either the bioactive agent is locally delivered to the endovascular wall injury, or a therapeutic dose of in particular a des-methyl tocopherol agent is delivered to the endovascular wall injury. In either case, the local delivery of bioactive agent is done in a manner sufficient to substantially stimulate or promote vascular wound healing.

According to one mode of this aspect, the vascular wound healing is induced or promoted by locally delivering the tocopherol agent to the site of the endovascular wall injury.

According to another mode, vascular wound healing is induced or promoted by delivering a therapeutic dose of a gamma-tocopherol agent, or a precursor, analog, or derivative thereof, to the endolumenal wall injury.

According to another mode, the tocopherol agent comprises a DNA plasmid encoding the production of the tocopherol agent, or a precursor, analog or derivative thereof.

According to another mode, the bioactive tocopherol agent comprises a viral or nonviral gene vector encoding production of such tocopherol molecule.

According to another mode, the bioactive tocopherol agent comprises gamma-tocopherol, or a precursor, analog, or derivative thereof.

According to another mode, the bioactive tocopherol agent is delivered to the site of the endolumenal wall injury by a stent that holds and releases the tocopherol agent.

In another mode, the tocopherol agent is delivered to the site of the endothelial wound by a drug-eluting angioplasty balloon.

Another aspect of the invention is a method for reducing restenosis in response to an endolumenal wall injury and includes implanting an endolumenal stent at a location along a wall of a lumen in a body of a patient in combination with administering a therapeutic dose of a bioactive agent that comprises at least one of a des-methyl tocopherol agent, a phytyl substituted chromanol agent, or a palm oil agent, in a manner providing a higher bioactivity of the bioactive agent at the location than elsewhere in the body and sufficient to reduce restenosis at the location following the stent implantation.

Another aspect of the invention is a method for reducing restenosis in response to an endolumenal wall injury that includes implanting an endolumenal stent at a location along a wall of a lumen in a body of a patient in combination with administering a dose of gamma-tocopherol to the patient in a manner that provides a higher bioactivity of the gamma-tocopherol at the location than elsewhere in the body and sufficient to reduce restenosis at the location following the stent implantation.

One mode of this aspect includes, in combination with the administration of gamma-tocopherol, administering a dose of an anti-restenosis agent in a manner that provides a higher bioactivity of the anti-restenosis agent at the location than elsewhere in the body and sufficient to inhibit restenosis at the location following the stent implantation.

According to one embodiment of this mode, the anti-restenosis agent delivered is at least one of sirolimus, tacrolimus, everolimus, ABT-578, paclitaxel, dexamethasone, 17-Beta-estradiol, steroid, des-aspartate angiotensin I (DAA-1), angiotensin converting enzyme inhibitor (ACE inhibitor), angiotensin II receptor blocker, tachykinin, sialokinin, apocynin, pleiotrophin, exochelin, an iron chelator, VEGF, heparin, coumadin, clopidogrel, IIb/IIIa inhibitor, nitric oxide, a nitric oxide donor, an eNOS antagonist, a nitric oxide synthesis promoter, a statin, or a precursor, analog, or derivative thereof, or a combination or blend thereof.

According to another embodiment, one of the gamma-tocopherol and the anti-restenosis agent is eluted from the implanted stent, and the other of the gamma-tocopherol and the anti-restenosis agent is delivered systemically.

According to another embodiment, at least one of the gamma-tocopherol and the anti-restenosis agent is delivered locally to the location.

According to another embodiment, both the gamma-tocopherol and the anti-restenosis agent are eluted from the implanted stent.

Another aspect of the invention is a method for treating a patient by locally delivering to a lumen wall in a patient a bioactive agent that comprises at least one of a des-methyl tocopherol, a phytyl substituted chromanol, and a palm oil agent.

Each of the aspects, modes, embodiments, variations, and features herein described is considered independently valuable and beneficial without requiring combination with the others, even to the extent such value may stem from its ability to provide for such combination. Notwithstanding the foregoing, the various combinations apparent to one of ordinary skill based upon review of this disclosure and other available information are also considered additional independent benefit and value contemplated hereunder.

Further objects and advantages of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawing which is for illustrative purposes only:

DETAILED DESCRIPTION OF THE INVENTION

Figure 1:
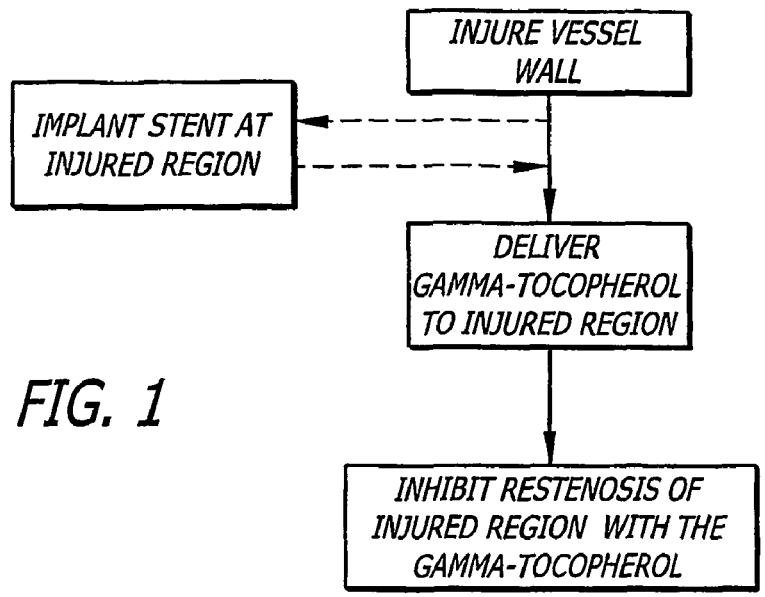
FIG. 1 shows a flow chart diagram of one embodiment according to the invention.

It is to be appreciated that the present disclosure provides various aspects, modes, embodiments, variations, and features thereof that provide enhanced medical therapy for lumenal wall disorders, and in particular in order to reduce restenosis related to stent implantation or other recanalization procedure. In particular, novel uses of gamma-tocopherol, and other related compounds, either alone or in various combinations, are herein provided in varying detail in order to achieve the various benefits and objects described.

Tocopherols, in general, have been the topic of substantial research and clinical experience as "GRAS" compounds sold over the counter for many different indications. Tocopherol is generally described according to Formula 1:

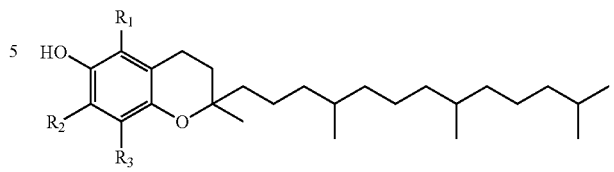

Formula 1 wherein the various homologues of this chemical structure are further characterized as to the various respective "R1-3" groups according to the following Table 1:

TABLE 1

| Tocopherol Homologues | | | |
|---|---|---|---|
| Homologues | R1 | R2 | R3 |
| Alpha-Tocopherol | CH3 | CH3 | CH3 |
| Beta-Tocopherol | CH3 | H | CH3 |
| Gamma-Tocopherol | H | CH3 | CH3 |
| Delta-Tocopherol | H | H | CH3 |

Natural Tocopherol generally exists as a mixture of the four homologues, Alpha, Beta, Gamma, and Delta—available as a mixed product typically referred to as "Mixed Tocopherol"—which is also the form often referred to as "Vitamin E." In other references, however, gamma-tocopherol is the major form of what is often referred to as "Vitamin E" in many plant seeds and in the typical US diet, whereas alpha-tocopherol is a more predominant form of what is often referred to as "Vitamin E" in tissues and supplements. In general, the gamma-tocopherol form has received less research and science attention than the alpha form of homologue. However, recent studies indicate that gamma-tocopherol may be important to human health and that it possesses unique features that distinguish it from alpha-tocopherol. Gamma-tocopherol appears to be a more effective trap for lipophilic electrophiles than is alpha-tocopherol. In addition, gamma-Tocopherol is well absorbed and accumulates to a significant degree in some human tissues; it is metabolized, however, largely to 2,7,8-trimethyl-2-(beta-carboxyethyl)-6-hydroxychroman (gamma-CEHC), which is mainly excreted in the urine. Gamma-CEHC, but not the corresponding metabolite derived from alpha-tocopherol, has natriuretic activity to which certain physiologic importance has been attributed. Both gamma-tocopherol, and gamma-CEHC, but not alpha-tocopherol, inhibit cyclooxygenase activity and, thus, possess and exhibit substantial anti-inflammatory properties. Some human and animal studies have indicated that plasma concentrations of gamma-tocopherol are inversely associated with the incidence of cardiovascular disease and prostate cancer. Furthermore, it has been shown that high doses of alpha-tocopherol deplete plasma and tissue levels of gamma-tocopherol, whereas in contrast gamma-tocopherol supplementation increases both the gamma and alpha forms.

The following Table 2 provides further illustration of certain data according to one publication related to certain biological and anti-oxidant activities of the various forms of tocopherol:

TABLE 2

Biologic and Antioxidant Activities of various tocopherols

| Kind of Tocopherol | Biological Activity (IU/mg) | Antioxidant Activity (d-Alpha-Toc = 100) |
|---|---|---|
| dl-ALpha-Tocopherol acet. | 1 | 0 |
| d-Alpha-Tocopherol acet. | 1.36 | 0 |
| dl-Alpha-Tocopherol | 1.1 | 100 |
| d-Alpha-Tocopherol | 1.49 | 100 |
| d-Beta-Tocopherol | 0.75 | 130 |
| d-Gamma-Tocopherol | 0.15 | 200 |
| d-Delta-Tocopherol | 0.05 | 300–500 |

NOTE:
dl-form = synthetic;
d-form = natural

Accordingly, various of the particular beneficial embodiments herein described utilize gamma-tocopherol—or precursors, analogs, or derivatives thereof, including for example in particular gamma-tocopherol's metabolite, gamma-CEHC—for local delivery to walls of vessels or other lumens in order to inhibit (e.g. prevent or reduce) restenosis associated with recanalization, stent implantation, or other invasive procedure. Various more particular embodiments will become apparent upon further description of the following.

The following information provides certain useful information variously related to either gamma-tocopherol, or other related compounds, so as to provide a better understanding of certain aspects, modes, and embodiments of the present invention.

According to one published study, the ability of alpha-tocopherol to reduce restenosis after angioplasty was tested in a rabbit model in which angioplasty was performed on established atherosclerotic lesions. Lesions induced by 4 wk of cholesterol feeding after focal desiccation of femoral arteries were balloon dilated. Three weeks after angioplasty, angiographically determined minimum luminal diameters were less in the untreated group (0.80+/−0.51 mm) than in the group treated with oral alpha-tocopherol beginning 19 d before angioplasty (1.38+/−0.29 mm; P<0.01). The cross-sectional area of the intima-media was greater in the untreated group (1.18+/−0.48 mm2) than in the alpha-tocopherol group (0.62+/−0.25 mm2, P<0.0001). These differences were not due to vasoconstriction or altered plasma cholesterol. Alpha-tocopherol thus reduced restenosis after angioplasty in this model. In rabbit vascular smooth muscle cells, oxidized low density lipoprotein stimulated DNA synthesis. Alpha-tocopherol treatment inhibited DNA synthesis stimulated by oxidized low density lipoprotein, but not by serum. The findings are consistent with the hypothesis that oxidized lipids can stimulate hyperplasia and that antioxidants may limit hyperplasia by inhibiting either the oxidation or the proliferative effects of oxidants on cells.

The omega-3 polyunsaturated fatty acids derived from fish oils have been shown to modulate many factors believed to affect the pathogenesis of atherosclerosis. Because certain features of restenosis following angioplasty mimic some of the early changes of atherogenesis, some researchers have suggested that fish oil might prevent restenosis following angioplasty. One group has reported the effects of omega-3 fatty acids on the rate of restenosis following percutaneous intraluminal coronary angioplasty (PTCA). More specifically, from August 1989 through September 1992, 551 patients were randomized to start receiving a daily dietary supplement of ten 1.0 g capsules containing 80.6% ethyl esters of omega-3 fatty acids providing 4.1 g eicosapentaenoic acid (EPA) and 2.8 g docosahexaenoic acid (DHA) for 6 months or an equal amount of an ethyl ester of corn oil. Four hundred seventy subjects who were well matched for risk factors completed successful angioplasty of one or multiple lesions in native coronary vessels and constituted the study cohort, of whom 447 were evaluable at 6 months after PTCA. The criteria for restenosis were that the quantitative coronary angiography at 6 months show a >30% increase in narrowing at the stenosis site or loss of at least half of the gain achieved at the time of PTCA and final restenosis with <50% luminal diameter remaining. In 93% of the patients, the end point was determined by angiography and in all except 1% of these by quantitative coronary angiography. Compliance with the fish oil supplement was good as judged by incorporation of EPA and DHA in plasma and red blood cell phospholipids. The restenosis rate among analyzable patients was 46% for corn oil and 52% for fish oil (P=0.37). The addition of 200 mg alpha-tocopherol for all subjects during the study had no effect on restenosis rates.

The foregoing was the largest of such trials at the time of that publication, and a supplement of 8 g/d of omega-3 fatty acids failed to prevent the usual high rate of restenosis after PTCA. No adverse effects were attributable to this large daily supplement of omega-3 fatty acids. Moreover, the addition of the 200 mg alpha-tocopherol to the subjects had no effect on restenosis rates and was an oral supplement of only one dosage. Moreover, this study did not evaluate the effects of gamma-tocopherol, which is considered to provide a substantial benefit according to various embodiments of the present invention.

Another published study tested whether alpha-tocopherol prevents restenosis following percutaneous transluminal coronary angioplasty (PTCA). According to this study, patients were enrolled in a double-blind, placebo-controlled trial. Patients were randomized after successful PTCA to receive vitamin E in the form of dl-alpha-tocopherol, 1200 IU/day, orally vs an inactive placebo for 4 months. Patients' blood was analyzed at baseline and at 4 months post-PTCA for differences in plasma lipids, lipoproteins, apolipoproteins, alpha-tocopherol, retinol, beta-carotene and lipoperoxide concentrations. One hundred patients completed the protocol. No significant difference was found in any parameter except alpha-tocopherol level between the vitamin E group and the placebo group, verifying compliance. Follow-up cardiac catheterization was obtained in 83% of the patients receiving placebo and in 86% of the patients receiving dl-alpha-tocopherol. Including thallium and exercise stress testing, objective information was obtained for practically all the patients receiving dl-alpha-tocopherol or placebo. Restenosis was defined as the presence of a lesion with greater than or equal to 50% stenosis in a previously dilated artery segment and results were analyzed with respect to pre- and post-PTCA artery diameter, vessel diameter at follow-up, and restenosis rate. Patients receiving di-alpha-tocopherol had a 35.5% restenosis (angiographically documented) vs 47.5% restenosis in patients receiving the placebo. The overall incidence of restenosis defined by an abnormal angiogram or thallium test or exercise stress test was 34.6% in patients receiving dl-alpha-tocopherol and 50% in patients receiving the placebo. This difference (p=0.06) did not reach significance, though believed to have reached such significance in the event a larger sample size were to produce similar comparative results.

Certain other evidence suggests oxidative stress may provide an important trigger in the complex chain of events leading to atherosclerosis. Randomized clinical trials have not provided, to date, definitive evidence of the beneficial effect of orally administered antioxidant vitamins. Problems associated with the use of vitamins include their potential pro-oxidant effects, and the decreased absorption of natural gamma-tocopherol caused by alpha-tocopherol supplements. Probucol and amlodipine have been suggested to provide more powerful lipophilic antioxidants than certain forms of vitamin E. They also do not appear to have significant pro-oxidant properties. Probucol has been shown to prevent coronary restenosis after balloon angioplasty in clinical trials. Its high density lipoprotein-lowering effect, however, prevents it from being protective against progression of coronary atherosclerosis. Slowing or reversing the atherosclerotic process with an antioxidant may by augmented by the use of a powerful lipophilic antioxidant that has neutral or positive effects on serum lipids when given alone or in combination with a lipid-lowering agent.

Another publication notes the following with respect to certain health aspects of palm oil, and in its further relation to tocopherols. Palm oil is an excellent choice for food manufacturers because of its nutritional benefits and versatility. The oil is highly structured in that it contains predominantly oleic acid at the sn2-position in the major triacylglycerols, accounting for the beneficial effects described in numerous nutritional studies. Oil quality and nutritional benefits have been assured for the variety of foods that can be manufactured from the oil directly or from blends with other oils while remaining free of trans-fatty acids. The oxidative stability coupled with the cost-effectiveness is unparalleled among cholesterol-free oils, and these values can be extended to blends of polyunsaturated oils to provide long shelf-life. Presently the supply of genetic-modification-free palm oil is assured at economic prices, since the oil palm is a perennial crop with unparalleled productivity. Numerous studies have confirmed the nutritional value of palm oil as a result of the high mono-unsaturation, in particular at the 2-position of the oil's triacylglycerols, making the oil as healthful as olive oil. It is now recognized that the contribution of dietary fats to blood lipids and cholesterol modulation is a consequence of the digestion, absorption, and metabolism of the fats. Lipolytic hydrolysis of palm oil glycerides containing predominantly oleic acid at the 2 position and palmitic and stearic acids at the 1 and 3 positions allows for the ready absorption of the 2-monoacrylglycerols while the saturated free fatty acids remain poorly absorbed.

Dietary palm oil in balanced diets generally reduces blood cholesterol, low-density lipoprotein (LDL) cholesterol, and triglycerides while raising the high-density lipoprotein (HDL) cholesterol. Improved lipoprotein(a) and apo-A1 levels were also demonstrated from palm oil diets. Important benefit also comes from the lowering of blood triglycerides (or reduced fat storage) as compared with those from polyunsaturated fat diets. Virgin palm oil also provides carotenes apart from tocotrienols and tocopherols that have been shown to be powerful antioxidants and potential mediators of cellular functions. These compounds can be antithrombotic, cause an increase of the prostacyclin/thromboxane ratio, reduce restenosis, and inhibit HMG-CoA-reductase (thus reducing) cholesterol biosynthesis. Red palm oil is in particular a rich source of beta-carotene as well as of alpha-tocopherol and tocotrienols.

While gamma-tocopherol is of particular interest and benefit according to the present invention, compounds such as certain palm oils, certain forms of omega-3-fatty acids, e.g. Probucol, etc., as just described above, and related components thereof may also provide benefit in therapeutic doses adjunctive to recanalization or stenting procedures, either alone or in combination with gamma-tocopherol.

Further more detailed examples of studies and/or publications related to the information cited above are variously disclosed in the following publications:
(1) Godfried et al., Potentiation of Atherosclerotic lesion in rabbits by a high dietary level of vitamin E, *British Journal of Nutrition*, 61:607-617, 1989;
(2) DeMaio S J, King S B 3rd, Lembo N J, Roubin G S, Hearn J A, Bhagavan H N, Sgoutas D S., Vitamin E supplementation, plasma lipids and incidence of restenosis after percutaneous transluminal coronary angioplasty (PTCA), *J Am Coll Nutr.*, 1992 February; 11(1):68-73. (Andreas Gruentzig Cardiovascular Center, Department of Internal Medicine (Cardiology), Atlanta, Ga.);
(3) Ferns et al., Probucol inhibits neointimal thickening and macrophage accumulation after balloon injury in the cholesterol-fed rabbit, *Proc. Natl. Acad. Sci.*, 89:11312-11316, December 1992;
(4) Freyschuss et al., Antioxidant Treatment Inhibits the Development of Intimal Thickening after Balloon Injury of the Aorta in Hypercholesterolemic Rabbits, *J. Clin. Invest.*, 91:1282-1288, 1993;
(5) Schneider et al., Probucol Decreases Neointimal Formation in a Swine Model of Coronary Artery Balloon Injury, *Basic Science Report*, 88:628-637, 1993;
(6) Blann et al., Free radicals, antioxidants, and endothelial cell damage after percutaneous translumenal coronary angioplasty, *Coronary Artery Disease*, (1993), vol. 4, pp. 905-910;
(7) Leaf A, Jorgensen M B, Jacobs A K, Cote G, Schoenfeld D A, Scheer J, Weiner B H, Slack J D, Kellett M A, Raizner A E, et al., "Do fish oils prevent restenosis after coronary angioplasty?" *Circulation*, 1994 November; 90(5):2248-57. (Massachusetts General Hospital, Charlestown 02129);
(8) Konneh et al., Vitamin E inhibits the intimal response to Balloon catheter injury in the carotid artery of the cholesterol-fed rat, *Atherosclerosis*, 113:29-39, 1995;
(9) Nunes et al., Combination of Vitamins C and E Alters the Response to Coronary Balloon Injury in the Pig, *Arteriosclerosis, Thrombosis, and Vascular Biology*, (1995), vol. 15, No. 1, pp. 156-165;
(10) Lafont A M, Chai Y C, Cornhill J F, Whitlow P L, Howe P H, Chisolm G M, Effect of alpha-tocopherol on restenosis after angioplasty in a model of experimental atherosclerosis., *J. Clin. Invest.*, 1995 March; 95(3):1018-25;
(11) Tardif et al., Probucol and Multivitamins in the Prevention of Restenosis after Coronary Angioplasty, *The New England Journal of Medicine*, 320:365-372, 1997;
(12) Rodes J, Cote B, Lesperance J, Bourassa M G, Doucet S, Bilodeau L, Bertrand O F, Harel F, Gallo R, Tardif J C, Prevention of restenosis after angioplasty in small coronary arteries with probucol., *Circulation*, 1998 Feb. 10; 97(5):429-36;
(13) Tardif, J C., Insights into oxidative stress and atherosclerosis, *Can. J. Cardiol.*, 2000 July; 16 Suppl D:2D-4D (Montreal Heart Institute, Montreal, Canada);
(14) Jiang Q, Christen S, Shigenaga M K, Ames B N, "gamma-tocopherol, the major form of vitamin E in the US diet, deserves more attention," *Am. J. Clin. Nutr.*, 2001 December; 74(6):714-22;
(15) Ong A S, Goh S H, Palm oil: a healthful and cost-effective dietary component, *Food Nutr. Bull.*, 2002 March; 23(1):11-22. (Institute of Advanced Studies, University of Malaya, Kuala Lumpur, Malaysia);
(16) Tardiff J C, Gregoire J, L'Allier P L., Prevention of restenosis with antioxidants: mechanisms and implications, *Am J Cardiovasc Drugs*, 2002; 2(5):323-34;

(17) Tardiff J C, "Clinical results with AGI-1067: a novel antioxidant vascular protectant." *Am. J. Cardiol.*, 2003 Feb. 6; 91(3A):41A-49A; and

(18) Deng Y M, Wu B J, Witting P K, Stocker R; Probucol protects against smooth muscle cell proliferation by upregulating heme oxygenase-1, *Circulation,* 2004 Sep. 28; 110(13):1855-60. Epub 2004 Sep. 13.

The disclosures of the foregoing cited published references are herein incorporated in their entirety by reference thereto.

While various of these disclosures differ in the particular molecules and agents being studied, and in the related study protocols, analysis, results, and conclusions, it is apparent that certain of the compounds described have some general benefit for treating atherosclerosis or restenosis. Where others had failed, such may be the result of the study design, e.g. dosing and delivery modality of the particular compounds. For example, systemic (e.g. IV) or oral dosing of such compounds may be subject to certain clearance, metabolism, or simple dilution aspects that render the treatment compounds ineffective.

Accordingly, in one regard the present invention responds to such shortcomings by incorporating such compounds in novel delivery modalities to maximize the local potency and bioactivity at the site of injury, e.g. vascular injury related to restenosis, or in the setting of treating atherosclerosis (including for example as prophylaxis of vulnerable plaque, which indication had not been disclosed or investigated in these prior studies). Local dosing, such as through needle injection catheters, or local end-hole or side-hole injection catheters, may provide necessary local concentrations to accomplish the objective of substantial reduction in atherosclerosis in one regard, or restenosis in another regard (or prophylaxis or therapy of vulnerable plaque in another regard). Of particular benefit, incorporating such compounds into or onto drug eluting stents for local elution directly into the subject endolumenal wall is considered a highly beneficial embodiment. In further embodiments, systemic dosing of such compounds is accomplished via complexing the particular molecules with "pro-drug" technologies, which deliver and provide the desired bioactivity only in local target cells such as injured vessel wall lining.

In another regard, certain of the prior studies observed the effects of alpha-tocopherol in the setting of restenosis. However, in particular beneficial embodiments of the present invention, gamma-tocopherol as a distinctly different form of Vitamin E has very different bioactivity and metabolism profiles and is the agent that is instead delivered to lumenal walls according to the novel methods herein described. For example, the combination of an implantable stent with local delivery of gamma-tocopherol, e.g. via a stent coating, wells or pores in the stent, concomitant local injection, etc., is considered of particular benefit. In particular, it is considered a highly safe and untraumatic approach to preventing restenosis using local delivery or elution of gamma-tocopherol as a GRAS compound.

In still a further regard, gamma-tocopherol has been observed to have pronounced synergistic effects with other compounds for improved healing and safe therapies. In particular, certain embodiments combine local delivery of gamma-tocopherol with other anti-proliferative, pro-healing (e.g. certain growth factors), anti-thrombotic or platelet adhesion, or anti-inflammatory compounds. More specific examples include sirolimus, tacrolimus, everolimus, paclitaxel, dexamethasone, 17-Beta-estradiol (or other steroid), des-aspartate angiotensin I, angiotensin II converting enzyme inhibitor (ACE inhibitor), angiotensin II receptor blocker, tachykinin (including in particular for example sialokinin or mosquito salivary tachykinin), apocynin, pleiotrophin, exochelin (or other iron chelators), VEGF, heparin, coumadin, clopidogrel, IIb/IIIa inhibitors, nitric oxide, nitric oxide donors, eNOS antagonists, statins, or pro-drugs or precursors thereof, or analogs or derivatives thereof, or further combinations or blends thereof.

Such combination is provided in a manner to provide for beneficial synergistic results providing therapies with safer and/or more efficacious results. In one particular regard for example, such anti-proliferative compounds delivered at doses that might otherwise have certain local toxicities in the area, e.g. sirolimus or paclitaxel, would gain substantial benefit by the synergistic healing activities of gamma-tocopherol, in particular but not limited to the extent it provides a highly safe and beneficial GRAS-type of additive. Generally well accepted studies and protocols have been published and are well know to characterize and optimize such benefits from particular combinations.

These include, for example, $IC_{50}$ cell culture studies and accompanying analytical techniques to evaluate the effects on the target cell cultures (e.g. vascular smooth muscle cells or endothelium) across sample concentration variants of the combination agents. Such studies may be thereafter followed by small mammal (e.g. rat/rabbit) and/or larger mammal (e.g. pig) pre-clinical studies evaluating the tissue responses in-vivo in the intended treatment conditions. These pre-clinical animal screening studies are thereafter followed by controlled human clinical trials. Each such exemplary stage of development may in itself include multiple iterations to optimize results in the normal course of development. Moreover, information learned at each phase may be usefully employed to determine the proper parameters for entering the next stage of screening for development. For example, where optimal tissue doses are determined in $IC_{50}$ studies, these may be correlated with a range of stent elution doses to evaluate in animal implant studies. In further examples, prior published results of other drugs, e.g. sirolimus or tacrolimus, provide certain correlates from $IC_{50}$ results to optimized stent elution dosing on a "per millimeter tissue" or "per millimeter stent" basis as a helpful guide for an initial range for testing.

Such characterization and optimization testing, and use of correlates in extending from one phase of development for local agent delivery to another phase, may be performed to further characterize and optimize single agent protocols, as well as combination agent protocols. These may be performed for example with respect to gamma-tocopherol either by itself or in various combination with other agents as herein described by way of certain beneficial examples.

Whereas the present embodiments are considered of particular benefit for treating vascular restenosis, such as in the coronary or peripheral arteries, other vessels or lumens than blood vessels are contemplated as indicated regions of the body where therapeutic uses of the present invention may be employed. Examples include the biliary duct, pancreatic duct, urethra, fallopian tubes, etc., to the extent wound healing of the vessel lining is therapeutic with gamma-tocopherol and/or other compounds and related therapies and delivery modalities herein described.

With particular further respect to in-stent restenosis (ISR), for the sake of this disclosure these terms are intended to further include "in-segment restenosis", generally considered to include restenotic scarring within about 5 mm beyond either end of the stent. As mentioned throughout this disclosure, a highly beneficial treatment (or prophylaxis) for ISR, is provided via a gamma-tocopherol eluting stent, either as a sole bioactive agent or in combination with other agents such as the illustrative examples herein described.

FIG. 1 shows a flow diagram of one embodiment of the invention for delivering gamma-tocopherol, or an analog or derivative thereof, to an injured region of a blood vessel in order to inhibit restenosis. This may be done in conjunction with stenting, shown in dashed line, which stenting may be the procedure by which the injury is made or adjunctive thereto, e.g. after atherectomy or predilation via angioplasty.

Figure 2:
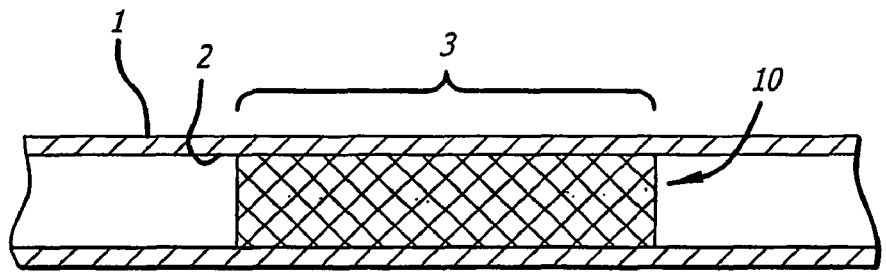
FIG. 2 shows a stented region of an artery according to one mode of the invention useful for example according to the embodiment shown in FIG. 1.
Figure 3:
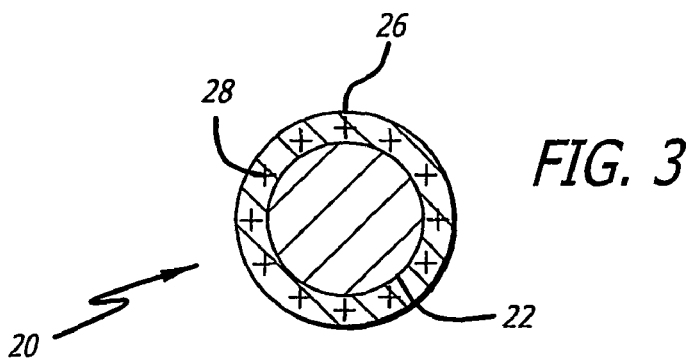
FIG. 3 shows a cross section of a stent strut coated with gamma-tocopherol according to another embodiment of the invention useful for example according to the embodiments shown in FIGS. 1 and 2.

FIG. 2 shows a schematic representation of an artery 1 which is stented with a stent 10 along a stented region 3. The endolumenal vessel lining 2 is typically denuded along the stented region 3. The stent 10 is endothelialized, and the vessel lining 2 is re-endothelialized, while smooth muscle cell hyperproliferation is inhibited, at least in part by way of delivery of the gamma-tocopherol to the region. In a highly beneficial mode shown in cross-section in FIG. 3, the gamma-tocopherol agent 28 is incorporated onto the stent 10 in a coating 26 located over underlying stent strut 22. Or, wells may be formed within the stent strut as a reservoir (not shown), or other modes may be used as apparent to one of ordinary skill. Or, the agent delivery may be accomplished via local delivery in the vessel, e.g. through an endhole or sidehole injection catheter, or via needle injection catheter, such as being investigated and previously disclosed by Endobionics corporation. Various coatings may be incorporated for use with such agent elution from stents, including porous polymers, biodegradable or bioerodable coatings (further including certain types of polymers or hydrogels for example), porous ceramics, or porous metal matrixes including porous electroless electrochemical deposition such as for example incorporating nickel-phosphorous or cobalt-phosphorous nanoporous composite depositions as has been previously published. However, incorporation of the gamma-tocopherol, and/or other related compounds as herein described, into such compositions is further contemplated as an additional beneficial embodiment of the present invention. Such includes for the particular uses in conjunction with stents, or other uses as bioactive agent-eluting implant surfaces.

The disclosures in the following issued U.S. Patent Nos. are herein incorporated in their entirety by reference thereto: U.S. Pat. No. 5,512,595 to Regnier et al.; U.S. Pat. No. 5,627,205 to Regnier et al.; U.S. Pat. No. 5,957,975 to Lafont et al.; U.S. Pat. No. 6,103,753 to Cynshi et al.; U.S. Pat. No. 6,221,904 to Agus et al.; U.S. Pat. No. 6,262,111 to Agus et al.; U.S. Pat. No. 6,420,420 to Agus et al.; U.S. Pat. No. 6,440,999 to Cynshi et al.; U.S. Pat. No. 6,608,106 to Agus et al.

The disclosures in the following issued U.S. Patent Nos. are also herein incorporated in their entirety by reference thereto: U.S. Pat. No. 4,144,325 to Voyt; U.S. Pat. No. 4,789,554 to Scavone et al.; U.S. Pat. No. 5,132,121 to Orfan et al.; U.S. Pat. No. 5,139,796 to Barkalow et al.; U.S. Pat. No. 5,200,213 to Orfan et al.; U.S. Pat. No. 5,200,214 to Barkalow et al.; U.S. Pat. No. 5,270,060 to Foster et al.; U.S. Pat. No. 6,048,891 to Wechter; U.S. Pat. No. 6,242,479 to Wechter; U.S. Pat. No. 6,262,279 to Hyatt; U.S. Pat. No. 6,346,544 to Hensley et al.; U.S. Pat. No. 6,410,589 to Wechter; U.S. Pat. No. 6,555,575 to Wechter; and U.S. Pat. No. 6,780,886 to Kondo et al.

The disclosures in the following Published International PCT Patent Applications are also herein incorporated in their entirety by reference thereto (and by reference to named inventors): WO 02/063022 to Van Eenennaam et al.; WO 2003/089452 to Li et al.; WO 2004/047732 to Ames et al.; and WO 2004/081215 to Pineda Priego et al.

The disclosures in the following Published U.S. Patent Applications are also herein incorporated in their entirety by reference thereto: US 2001/0031782 to Wechter; US 2001/0044462 to Hensley et al.; US 2002/0006954 to Hensley et al.; US 2002/0165268 to Wechter; US 2003/0166205 to Van Eenennaam; US 2003/0233672 to Li et al.; US 2004/0102385 to Ames et al.; US 2004/0102421 to Ames et al.; US 2004/0029954 to Wechter; US 2004/0058987 to Wechter; and US 2004/0091990 to Li et al.

The disclosures of all the articles and issued or published patent references provided above are herein incorporated in their entirety by reference thereto.

Gamma-tocopherol is herein described as a highly beneficial aspect of the invention, though other analogs or derivatives thereof may be used and contemplated within the intended scope of various aspects of the invention. For example, similar bioactivity as is known for gamma-tocopherol may be achieved with modifications to the specific molecule without departing from the intended scope of such aspects. In one regard, active sites and molecular regions or shapes, etc., associated therewith may be incorporated onto other molecular chains and provide further aspects of the invention. Pre-cursors such as pro-drugs are contemplated. Metabolites are also contemplated, such as for example gamma-CEHC (also referred to as "LLU-alpha", related to Loma Linda University work in the area) as a bioactive metabolite of gamma-tocopherol.

While gamma-tocopherol has been described according to highly beneficial embodiments hereunder, it is to be appreciated that this embodiment is illustrative of certain broader aspects, and furthermore that certain modifications may be made according to still further highly beneficial embodiments.

In one regard, gamma-tocopherol is one illustrative example of a broader group of "des-methyl tocopherols." This contemplated scope of compound would exclude alpha-tocopherol, but include for example other des-methyl forms of tocopherol, and in particular delta-tocopherol which also has a particular high anti-oxidant activity.

In another regard, gamma-tocopherol is one illustrative example of "phytyl substituted chromanols" as another broader group or class of compounds contemplated hereunder. This group would also include as further examples delta-tocopherol, and certain tocotrienols such as in particular gamma- or delta-tocotrienols. With regards to tocotrienols, these are generally represented by Formula 2 (provided for illustration with respect to the 'alpha' form, with similar substitutions between R groups for the respective alpha, beta, gamma, delta forms as provided for tocopherols in Table 1):

Formula 2

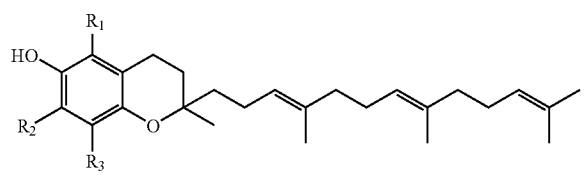

Tocotrienols penetrate tissues rapidly, including into the skin, and efficiently combat damage from UV. Antioxidant activity of tocotrienols is higher than that of tocopherols, but their concentration in the blood in normal physiologic conditions is much lower. Tocotrienols have beneficial effects in cardiovascular disease in particular, in part because they protect LDL from oxidation, and in part because they reduce the activity of fHMG-CoA reductase, a key enzyme to cholesterol synthesis. Like tocopherols, it is in particular beneficial according to further embodiments of the invention to incorporate des-methyl forms of tocotrienol, and in particular gamma-tocotrienol (though also in combination or alternative delta-tocotrienol), into the devices, systems, and methods herein described. Such may be done alone, or in combination with other active agents.

The following published PCT Patent Application is herein incorporated in its entirety by reference thereto: WO 99/25336 to Lane et al. as inventors.

These various groups of compounds herein described, and moreover the exemplary specific types specifically described immediately above (and the analogs or derivatives thereof, including without limitation precursor pro-drugs or metabolites), are considered as further aspects and embodiments hereof. This is in particular the case with respect to providing therapeutic use in treating lumenal wall disorders, and still more specifically via local delivery of agents, and still more specifically to treat restenosis including in the highly beneficial mode via stent elution for delivery.

The various compounds herein described, such as in particular gamma-tocopherol, are generally available for purchase, or may be otherwise manufactured or otherwise produced or prepared, using various known methods. Such for example may include purchasing or producing such agents in substantially purified form, or in combination with other agents or additives or byproducts of manufacture, which may be later purified or used in such combination form according to the embodiments herein described.

The present disclosure should be read in conjunction with the various disclosures of the following additional published patent applications, which are herein incorporated in their entirety by reference thereto: US 2003/0060873 to Gertner et al.; US 2003/0207933 to Wang et al.; US 2004/0057945 to Maier et al.; WO 2003/045582 to Gertner et al.; WO 2004/000208 to Maier et al.; WO 2004/028571 to Peacock et al.; WO 2004/069201 to Wang et al.

In addition, the following issued patents are also herein incorporate in their entirety by reference thereto: U.S. Pat. Nos. 5,843,937; 6,100,237, and 6,759,416.

The following pending and co-owned US Patent Applications are also herein incorporated in their entirety by reference thereto (e.g. by reference to U.S. Ser. Nos.): Ser. No. 10/701,262 filed Nov. 3, 2003 by Klein et al.; Ser. No. 10/724,453 filed Nov. 28, 2003 by Peacock et al.; 60/607,884 filed Sep. 8, 2004 to Larrick; and 60/607,832 filed Sep. 8, 2004 to Lee et al.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for treating a patient, comprising:
   delivering an angioplasty balloon to a site along a lumen in the patient;
   inflating the balloon to contact a wall of the lumen at the site; and
   locally delivering to the lumen wall at the site a volume of des-methyl tocopherol, or a precursor, analog, or derivative thereof.

2. The method of claim 1, wherein the des-methyl tocopherol is a gamma-tocopherol agent.

3. The method of claim 1, wherein said volume comprises a precursor of the des-methyl tocopherol that comprises a DNA plasmid encoding the production of the des-methyl tocopherol.

4. The method of claim 1, wherein said volume comprises a precursor of the des-methyl tocopherol that comprises a viral or non-viral gene vector encoding the production of the des-methyl tocopherol.

5. The method of claim 1, further comprising:
   delivering an endolumenal stent to the site;
   deploying the stent to contact the wall at the site; and
   delivering the volume into the wall at the site from the deployed stent.

6. The method of claim 5, further comprising:
   coating or adsorbing the stent with a delivery carrier containing the volume; and
   delivering the volume to the wall at the site via release from the delivery carrier.

7. The method of claim 1, further comprising:
   coupling said volume to the angioplasty balloon; and
   delivering said volume to the wall at the site by releasing the volume from the angioplasty balloon.

8. The method of claim 1, further comprising:
   administering a therapeutic dose of the des-methyl tocopherol in said volume in a manner providing a higher bioactivity of the des-methyl tocopherol at said site than elsewhere in the body.

9. The method of claim 1, further comprising:
   in combination with said volume of des-methyl tocopherol, delivering into the wall at the site a therapeutic dose of a second bioactive agent that is different from the des-methyl tocopherol.

10. The method of claim 9, wherein said second bioactive agent comprises an anti-restenosis agent delivered in a manner that provides a higher bioactivity at said site than elsewhere in the body.

11. The method of claim 10, wherein said dose of antirestenosis agent is delivered in a manner sufficient to inhibit restenosis at said site following balloon angioplasty or stent implantation.

12. The method of claim 10, wherein said antirestenosis agent comprises at least one agent selected from the group consisting of sirolimus, tacrolimus, everolimus, ABT-578, paclitaxel, dexamethasone, 17-betaestradiol, steroid, des-aspartate angiotensin I (DAA-1), angiotensin converting enzyme inhibitor (ACE inhibitor), angiotensin II receptor blocker, tachykinin, sialokinin, apocynin, pleiotrophin, exochelin, an iron chelator, VEGF, heparin, coumadin, clopidogrel, IIb/IIIa inhibitor, nitric oxide, a nitric oxide donor, an eNOS antagonist, a nitric oxide synthesis promoter, and a statin, or a precursor, analog, or derivative thereof, or a combination or blend thereof.

13. The method of claim 9, further comprising:
locally delivering the first bioactive agent and second bioactive agent into the wall at the site.

14. The method of claim 12, further comprising:
eluting at least one of the des-methyl tocopherol and said second bioactive agent from the angioplasty balloon or an implanted stent into the wall at the site.

15. The method of claim 12, further comprising:
systemically delivering the other of the des-methyl tocopherol and the second bioactive agent.

16. The method of claim 9, further comprising:
eluting both the des-methyl tocopherol and the second bioactive agent from the angioplasty balloon or an implanted stent.

17. The method of claim 9, further comprising:
coating an implantable endolumenal stent with a porous non-polymeric carrier matrix;
holding the volume of des-methyl tocopherol principally within the porous metal carrier matrix;
delivering and deploying the stent to contact the wall at the site; and
eluting the volume from the matrix into the wall at the site from the deployed stent.

18. A system for treating a patient, comprising:
an angioplasty balloon that is deliverable to a site along a lumen in a patient and is inflatable to contact a wall of the lumen at the site;
a volume of a pharmaceutically acceptable preparation of des-methyl tocopherol, or a precursor, analog, or derivative thereof; and
a local drug delivery system coupled to the volume and configured to deliver the volume to the lumen wall at the site.

19. The system of claim 18, wherein:
said local drug delivery system comprises a carrier coupling the volume to at least one of the angioplasty balloon and an implantable endolumenal stent;
said volume is held and deliverable to the wall at the site via release from the carrier.

* * * * *